(12) United States Patent
Gupta et al.

(10) Patent No.: US 10,426,551 B2
(45) Date of Patent: Oct. 1, 2019

(54) PERSONALIZED REFRACTIVE SURGERY RECOMMENDATIONS FOR EYE PATIENTS

(71) Applicant: Microsoft Technology Licensing, LLC, Redmond, WA (US)

(72) Inventors: Manish Gupta, Hyderabad (IN); Prashant Gupta, Hyderabad (IN); Joy Mustafi, Hyderabad (IN)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 37 days.

(21) Appl. No.: 15/418,574

(22) Filed: Jan. 27, 2017

(65) Prior Publication Data
US 2018/0161098 A1    Jun. 14, 2018

(30) Foreign Application Priority Data
Dec. 9, 2016   (IN) .............................. 201641042226

(51) Int. Cl.
*A61B 34/10*   (2016.01)
*A61F 9/008*   (2006.01)
(Continued)

(52) U.S. Cl.
CPC ........ *A61B 34/10* (2016.02); *A61B 2034/105* (2016.02); *A61F 9/008* (2013.01);
(Continued)

(58) Field of Classification Search
CPC .... A61B 34/10; A61B 2034/105; G06N 3/08; A61F 9/008; A61F 2009/00878
See application file for complete search history.

(56) References Cited

U.S. PATENT DOCUMENTS 8,273,077 B2    9/2012  MacRae et al.
8,346,518 B2 *  1/2013  Dupps, Jr. .............. G06F 19/12
                                                         703/6
(Continued)

FOREIGN PATENT DOCUMENTS

CA    2416598 A1    1/2002
EP    1666009 A2    6/2006

OTHER PUBLICATIONS

Aaron, et al., "Preoperative Factors Predict Postoperative Changes in Visual Acuity for Myopic Laser Refractive Surgery Patients", In Journal of Investigative Ophthalmology & Visual Science, vol. 50, Issue 13, Apr. 2009, 2 pages.

(Continued)

*Primary Examiner* — Cuong B Nguyen
(74) *Attorney, Agent, or Firm* — Ray Quinney & Nebeker, P.C.; Thomas M. Hardman; Stephen A. Wight

(57) ABSTRACT

Aspects extend to methods, systems, and computer program products for providing personalized surgery recommendations for eye patients. Surgery types, and surgery parameters can be recommended for a patient based on predicted post-operative UCVA for the patient if the surgery types and surgery parameters were to be used. Predicting post-operative UCVA can be handled as a regression problem based on patient demography and pre-operative examination details. In an additional aspect, surgery parameters are automatically determined and/or optimized for improved post-operative UCVA by including surgery parameters in a regression model.

20 Claims, 3 Drawing Sheets

(51) Int. Cl.
*G06N 5/00* (2006.01)
*G06N 20/00* (2019.01)
(52) U.S. Cl.
CPC .... *A61F 2009/00878* (2013.01); *G06N 5/003* (2013.01); *G06N 20/00* (2019.01)

(56) References Cited

U.S. PATENT DOCUMENTS

| | | | |
|---|---|---|---|
| 8,414,565 | B2 | 4/2013 | Roberts et al. |
| 9,501,621 | B2* | 11/2016 | Dai ..................... A61F 9/00804 |
| 2012/0172854 | A1* | 7/2012 | Raymond ............... A61F 9/008 606/5 |
| 2012/0245484 | A1 | 9/2012 | McClatchey et al. |

OTHER PUBLICATIONS

Aaron, et al., "Why Preoperative Acuity Predicts Postoperative Acuity in Wavefront-Guided LASIK", In Journal of Optometry and Vision Science, Nov. 2010, pp. 1-7.
Fraccaro, et al., "Combining macula clinical signs and patient characteristics for age-related macular degeneration diagnosis: a machine learning approach", In BMC Ophthalmology, Jan. 27, 2015, pp. 1-19.
Kaiser, Jiri, "Algorithm for Missing Values Imputation in Categorical Data with Use of Association Rules", In Journal of the Computing Research Repository, Nov. 2012, 4 pages.
Young, Matt, "Statistics explain LASIK post-op acuity", http://www.eyeworld.org/article-statistics-explain-lasik-post-pp-acuity, Feb. 2011, pp. 1-2.
M. Najjar, "LASIK Risk Score: An Easy Method to Predict Postoperative Outcome", In Journal of Refractive Surgery, vol. 21, Jul. 2005, 2 pages.
Tanna, et al., "Femtosecond Laser Versus Mechanical Microkeratome: A Retrospective Comparison of Visual Outcomes at 3 Months", In Journal of Refractive Surgery, vol. 25, Jul. 2009, 4 pages.
Pieramici, et al., "Preoperative Evaluation for LASIK Surgery", http://eyewiki.aao.org/Preoperative_Evaluation_for_LASIK_Surgery, Retrieved Date: Sep. 21, 2016, pp. 1-5.
Piñero, et al., "PresbyMax: Presbyopia Correction by Multifocal LASIK", In Cataract & Refractive Surgery Today Europe, Jan. 2009, pp. 1-8.
Applegate, et al., "Visual Acuity as a Function of Zernike Mode and Level of Root Mean Square Error", In Journal of Optometry and Vision Science, vol. 80, No. 2, Feb. 2003, pp. 97-105.
Roy, et al., "Dynamic Hierarchical Classification for Patient Risk-of-Readmission", In Proceedings of the 21th ACM SIGKDD International Conference on Knowledge Discovery and Data Mining, Aug. 10, 2015, pp. 1691-1700.
Caballero, et al., "Dynamically Modeling Patient's Health State from Electronic Medical Records: A Time Series Approach", In Proceedings of the 21th ACM SIGKDD International Conference on Knowledge Discovery and Data Mining, Aug. 10, 2015, 69-78 pages.
Caruana, et al., "Intelligible Models for HealthCare: Predicting Pneumonia Risk and Hospital 30-day Readmission", In Proceedings of the 21th ACM SIGKDD International Conference on Knowledge Discovery and Data Mining, Aug. 10, 2015, pp. 1721-1730.

Che, et al., "Deep Computational Phenotyping", In Proceedings of the 21th ACM SIGKDD International Conference on Knowledge Discovery and Data Mining, Aug. 10, 2015, pp. 507-516.
Cheng, et al., "Predicting Subjective Judgment of Best Focus with Objective Image Quality Metrics", In Journal of Vision, vol. 4, Issue 4, Apr. 2004, pp. 310-321.
Fan, et al., "Hierarchical Graph-Coupled HMMs for Heterogeneous Personalized Health Data", In Proceedings of the 21th ACM SIGKDD International Conference on Knowledge Discovery and Data Mining, Aug. 10, 2015, pp. 239-248.
Ghassemi, et al., "Unfolding physiological state: Mortality modelling in intensive care units", In Proceedings of the 20th ACM SIGKDD international conference on Knowledge discovery and data mining, Aug. 24, 2014, pp. 75-84.
Guirao, et al., "A Method to Predict Refractive Errors from Wave Aberration Data", In Journal of Optometry & Vision Science vol. 80, No. 1, Jan. 1, 2003, pp. 36-42.
Hall, Mark A., "Correlation-based Feature Subset Selection for Machine Learning", In PhD thesis, University of Waikato, Apr. 1999, 198 pages.
Ho, et al., "Marble: High-throughput phenotyping from electronic health records via sparse nonnegative tensor factorization", In Proceedings of the 20th ACM SIGKDD international conference on Knowledge discovery and data mining, Aug. 24, 2014, pp. 115-124.
Liu, et al., "Temporal Phenotyping from Longitudinal Electronic Health Records: A Graph Based Framework", In Proceedings of the 21th ACM SIGKDD International Conference on Knowledge Discovery and Data Mining, Aug. 10, 2015, pp. 705-714.
Nori, et al., "Simultaneous Modeling of Multiple Diseases for Mortality Prediction in Acute Hospital Care", In Proceedings of the 21th ACM SIGKDD International Conference on Knowledge Discovery and Data Mining, Aug. 10, 2015, pp. 855-864.
Somanchi, et al., "Early Prediction of Cardiac Arrest (Code Blue) using Electronic Medical Records", In Proceedings of the 21th ACM SIGKDD International Conference on Knowledge Discovery and Data Mining, Aug. 10, 2015, pp. 2119-2126.
Thibos, et al., "Accuracy and Precision of Objective Refraction from Wavefront Aberrations", In Journal of Vision, vol. 4, Issue 4, Apr. 2004., pp. 1-8.
Watson, et al., "Predicting Visual Acuity from Wavefront Aberrations", In Journal of Vision, vol. 8, Issue 4, Apr. 22, 2008, pp. 1-19.
Applegate, et al., "Visual Acuity as a Function of Zernike Mode and Level of Root Mean Square Error. Optometry & Vision Science", In Journal Optometry and Vision Science, vol. 80, Issue No. 2, Feb. 2003, 9 Pages.
Azar, et al., "LASIK (Laser in Situ Keratomileusis): Fundamentals, Surgical Techniques, and Complications", By CRC Press, Nov. 26, 2002, 521 Pages.
Baron, et al., "Predicting Visual Performance following Excimer Photorefractive Keratectomy", In Journal of Refractive Surgery, vol. 8, Issue 5, Sep. 1, 1992.
Faulkner, Wade, "Laser Interferometric Prediction of Postoperative Visual Acuity in Patients with Cataracts", In American journal of ophthalmology, vol. 95, Issue 5, May 1, 1983, pp. 626-636.
Olsen, et al., "Predicting Visual Acuity in Children with Colobomas involving the Optic Nerve", In Journal of pediatric ophthalmology and strabismus, vol. 33, Issue 1, Jan. 1996, pp. 47-51.
Spurny, et al., "Instruments for Predicting Visual Acuity: A Clinical Comparison", In Journal of Archives of Ophthalmology, vol. 104, Issue 2, Feb. 1, 1986, pp. 196-200.

* cited by examiner

PERSONALIZED REFRACTIVE SURGERY RECOMMENDATIONS FOR EYE PATIENTS

CROSS-REFERENCE TO RELATED APPLICATIONS

This application claims priority to Indian National Application No. 201641042226, filed Dec. 9, 2016, and entitled "PERSONALIZED REFRACTIVE SURGERY RECOMMENDATIONS FOR EYE PATIENTS".

BACKGROUND

1. Background and Relevant Art

LASIK (Laser-Assisted in SItu Keratomileusis) surgeries are relatively popular for treatment of myopia (nearsightedness), hyperopia (farsightedness) and astigmatism. Millions of LASIK procedures have been performed worldwide. While many surgeries are successful, a relatively common side effect is a residual refractive error and poor uncorrected visual acuity (UCVA).

There are also a wide variety of different types of LASIK surgeries that can be performed. Often, any of a number of different types of LASIK surgery can be indicated to correct a vision problem. Each eye surgeon can prefer particular types of LASIK surgery over others and selection of LASIK type for a procedure is typically a manual process performed by the eye surgeon.

BRIEF SUMMARY

Examples extend to methods, systems, and computer program products for providing personalized refractive surgery recommendations for eye patients. A computer system accesses pre-operative eye characteristic data for the patient's eyes. The pre-operative eye characteristic data is taken from pre-operative diagnostic procedures performed on the patient. The computer system accesses demographic data for the patient.

The computer system inputs the pre-operative eye characteristic data and demographic data into a predictive model in the system memory. The predictive model having been formulated from other patient data for a plurality of other patients that previously had refractive surgery. The other patient data includes, for each other patient included in the plurality of other patients, one or more of: pre-operative eye characteristic data, demographic data, a refractive surgery type, and one or more post-operative uncorrected visual acuity (UCVA) values. Each of the one or more pre-operative uncorrected visual acuity (UCVA) values having been measured at a different post-operative time after refractive surgery The predictive model transforms the pre-operative eye characteristic data, demographic data, and other patient data through linear regression. Using linear regression, the predictive model predicts one or more post-operative uncorrected visual acuity (UCVA) maps for the patient. Each of the one or more post-operative uncorrected visual acuity (UCVA) maps is inferred for a corresponding refractive surgery type based on the patient's pre-operative eye characteristic data and demographic data in view of the other patient data. Each uncorrected visual acuity (UCVA) map predicts post-operative uncorrected visual acuity (UCVA) values for the patient at one or more post-operative time periods for the corresponding refractive surgery type.

Using linear regression, the predictive model matches the patient to a selected refractive surgery type based on predicted post-operative uncorrected visual acuity (UCVA) values in the one or more uncorrected visual acuity (UCVA) maps for the patient. The predictive model recommends the selected refractive surgery type as the refractive surgery recommendation for the patient.

In one aspect, the predictive model also determines a set of surgery parameters for the selected refractive surgery type. The predictive model can recommend the set of surgery parameters along with the selected refractive surgery type in a recommendation.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by practice. The features and advantages may be realized and obtained by means of the instruments and combinations particularly pointed out in the appended claims. These and other features and advantages will become more fully apparent from the following description and appended claims, or may be learned by practice as set forth hereinafter.

BRIEF DESCRIPTION OF THE DRAWINGS

In order to describe the manner in which the above-recited and other advantages and features can be obtained, a more particular description will be rendered by reference to specific implementations thereof which are illustrated in the appended drawings. Understanding that these drawings depict only some implementations and are not therefore to be considered to be limiting of its scope, implementations will be described and explained with additional specificity and detail through the use of the accompanying drawings in which.

DETAILED DESCRIPTION

Figure 1:
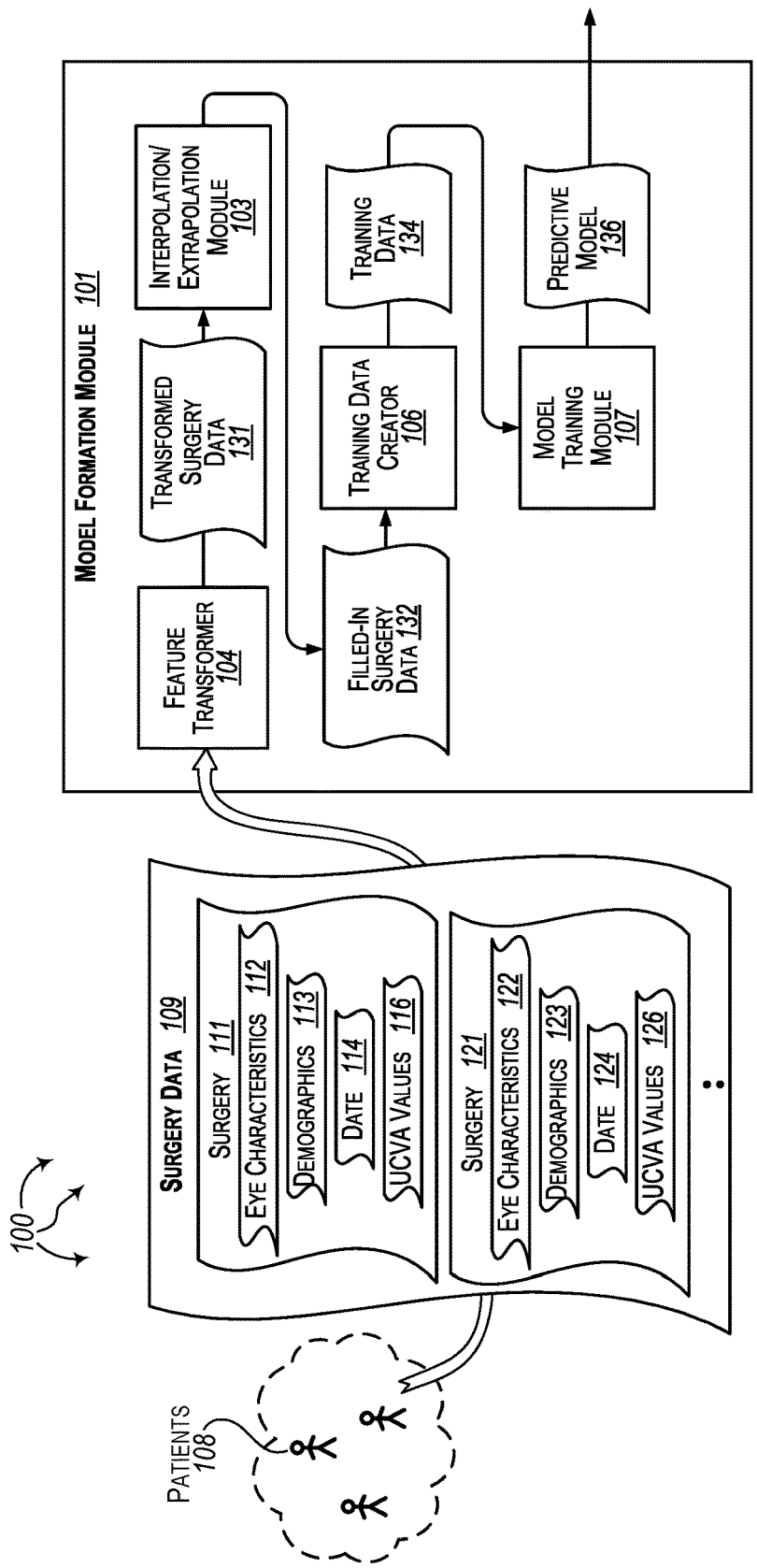
FIG. 1 illustrates an example computer architecture that facilitates formulating and training a predictive model to provide personalized refractive surgery recommendations for eye patients.

Examples extend to methods, systems, and computer program products for providing personalized refractive surgery recommendations for eye patients. A computer system accesses pre-operative eye characteristic data for the patient's eyes. The pre-operative eye characteristic data is taken from pre-operative diagnostic procedures performed on the patient. The computer system accesses demographic data for the patient.

The computer system inputs the pre-operative eye characteristic data and demographic data into a predictive model in the system memory. The predictive model having been formulated from other patient data for a plurality of other patients that previously had refractive surgery. The other patient data includes, for each other patient included in the plurality of other patients, one or more of: pre-operative eye characteristic data, demographic data, a refractive surgery type, and one or more post-operative uncorrected visual acuity (UCVA) values. Each of the one or more pre-operative uncorrected visual acuity (UCVA) values having been measured at a different post-operative time after refractive surgery The predictive model transforms the pre-operative eye characteristic data, demographic data, and other patient data through linear regression. Using linear regression, the predictive model predicts one or more post-operative uncorrected visual acuity (UCVA) maps for the patient. Each of the one or more post-operative uncorrected visual acuity (UCVA) maps is inferred for a corresponding refractive surgery type based on the patient's pre-operative eye characteristic data and demographic data in view of the other patient data. Each uncorrected visual acuity (UCVA) map predicts post-operative uncorrected visual acuity (UCVA) values for the patient at one or more post-operative time periods for the corresponding refractive surgery type.

Using linear regression, the predictive model matches the patient to a selected refractive surgery type based on predicted post-operative uncorrected visual acuity (UCVA) values in the one or more uncorrected visual acuity (UCVA) maps for the patient. The predictive model recommends the selected refractive surgery type as the refractive surgery recommendation for the patient.

In one aspect, the predictive model also determines a set of surgery parameters for the selected refractive surgery type. The predictive model can recommend the set of surgery parameters along with the selected refractive surgery type in a recommendation.

Implementations may comprise or utilize a special purpose or general-purpose computer including computer hardware, such as, for example, one or more computer and/or hardware processors (including Central Processing Units (CPUs) and/or Graphical Processing Units (GPUs)) and system memory, as discussed in greater detail below. Some computer systems can include and/or be (e.g., network) connected to eye examination devices for examining and/or mapping the human eye. Other devices are also discussed in greater detail below.

Implementations also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations can comprise at least two distinctly different kinds of computer-readable media: computer storage media (devices) and transmission media.

Computer storage media (devices) includes RAM, ROM, EEPROM, CD-ROM, Solid State Drives ("SSDs") (e.g., RAM-based or Flash-based), Shingled Magnetic Recording ("SMR") devices, Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

In one aspect, one or more processors are configured to execute instructions (e.g., computer-readable instructions, computer-executable instructions, etc.) to perform any of a plurality of described operations. The one or more processors can access information from system memory and/or store information in system memory. The one or more processors can (e.g., automatically) transform information between different formats, such as, for example, between any of: surgery data, eye characteristics, demographics, surgery types, surgery parameters, UCVA values, transformed surgery data, filled-in surgery data, training data, predictive models, UCVA maps, personalized refractive surgery recommendations, etc.

System memory can be coupled to the one or more processors and can store instructions (e.g., computer-readable instructions, computer-executable instructions, etc.) executed by the one or more processors. The system memory can also be configured to store any of a plurality of other types of data generated and/or transformed by the described components, such as, for example, surgery data, eye characteristics, demographics, surgery types, surgery parameters, UCVA values, transformed surgery data, filled-in surgery data, training data, predictive models, UCVA maps, personalized refractive surgery recommendations, etc.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, in response to execution at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the described aspects may be practiced in network computing environments with many types of computer system configurations, including, personal computers, desktop computers, laptop computers, message processors, hand-held devices, wearable devices, multicore processor systems, multi-processor systems, microprocessor-based or programmable consumer electronics, network PCs, minicomputers, mainframe computers, mobile telephones, PDAs, tablets, routers, switches, and the like. The described aspects may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. In another example, computer code is configured for execution in one or more processors, and may include hardware logic/electrical circuitry controlled by the computer code. These example devices are provided herein purposes of illustration, and are not intended to be limiting. Embodiments of the present disclosure may be implemented in further types of devices.

The described aspects can also be implemented in cloud computing environments. In this description and the following claims, "cloud computing" is defined as a model for enabling on-demand network access to a shared pool of configurable computing resources. For example, cloud computing can be employed in the marketplace to offer ubiquitous and convenient on-demand access to the shared pool of configurable computing resources (e.g., compute resources, networking resources, and storage resources). The shared pool of configurable computing resources can be provisioned via virtualization and released with low effort or service provider interaction, and then scaled accordingly.

A cloud computing model can be composed of various characteristics such as, for example, on-demand self-service, broad network access, resource pooling, rapid elasticity, measured service, and so forth. A cloud computing model can also expose various service models, such as, for example, Software as a Service ("SaaS"), Platform as a Service ("PaaS"), and Infrastructure as a Service ("IaaS"). A cloud computing model can also be deployed using different deployment models such as private cloud, community cloud, public cloud, hybrid cloud, and so forth. In this description and in the following claims, a "cloud computing environment" is an environment in which cloud computing is employed.

In this description and the following claims, "linear regression" is defined as an approach for modeling the relationship between a scalar dependent variable y and one or more explanatory variables (or independent variables) denoted X. Linear regression for one explanatory variable can be referred to as simple linear regression. Linear regression for multiple explanatory variables can be referred to as multiple linear regression.

In linear regression, relationships can be modeled using linear predictor models whose unknown model parameters are estimated from the data. For example, the conditional mean of y given the value of X is assumed to be an affine function of X. Less commonly, the median or some other quantile of the conditional distribution of y given X is expressed as a linear function of X. Similar to other regression analysis, linear regression can focuses on the conditional probability distribution of y given X, rather than on the joint probability distribution of y and X (which is instead the domain of multivariate analysis.)

Linear regression has a variety of uses. Linear regression can be used for prediction, forecasting, or error reductions. For example, linear regression can be used to fit a predictive model to an observed data set of y and X values. After developing such a model, if an additional value of X is then given without its accompanying value of y, the fitted model can be used to make a prediction of the value of y.

Linear regression models can include FastTree regression, FastRank (boosted decision trees) regression, Poisson regression, gradient tree bosting regression, online gradient descent based regression, and neural network based regression.

In this description and in the following claims, "sphere" is defined as the correction for nearsightedness or farsightedness being "spherical," or equal in all meridians of the eye. Sphere can indicate the amount of lens power (e.g., measured in diopters) prescribed to correct nearsightedness or farsightedness. A minus sign ('−') can be used to indicate correction of nearsightedness. A plus sign ('+') or no sign can be used to indicate correction of farsightedness.

In this description and in the following claims, "cylinder" is defined as the correction for astigmatism being not spherical. Instead the correction is shaped so one meridian has no added curvature, and the meridian perpendicular to this "no added power" meridian contains the maximum power and lens curvature to correct astigmatism. Cylinder can indicate the amount of lens power to correct astigmatism. A minus sign ('−') can be used to indicate correction of nearsighted astigmatism. A plus sign ('+') can be used to indicate correction of farsighted astigmatism.

In this description and in the following claims, "axis" is defined as orientation of the axis of the cylindrical lens. The direction of the axis is measured in degrees anticlockwise from a horizontal line drawn through the center of a pupil (the axis number can be different for each eye) when viewed from the front side of the glasses (i.e., when viewed from the point of view of the person making the measurement). It varies from 1 to 180 degrees.

In this description and in the following claims, "visual acuity" (or "VA") is defined as clarity of vision. Visual acuity is a measure of the spatial resolution of the visual processing system.

In this description and the following claims, "uncorrected visual acuity (or "UCVA") is defined as visual acuity without corrective lenses.

In this description and the following claims, "best corrected visual acuity (or "BCVA") is defined best achievable visual acuity with corrective lenses (e.g., glasses or contacts).

In this description and in the following claims, "OD" represents an abbreviation for oculus dexter, which is latin for right eye.

In this description and in the following claims, "OS" represents an abbreviation for oculus sinister, which is latin for left eye.

In this description and in the following claim, "laser eye surgery" is defined as any surgical procedure using a laser for the correction of myopia, hyperopia, or astigmatism. In general, laser eye surgery includes: Laser-Assisted in SItu Keratomileusis ("LASIK"), Advanced Surface Laser ("ASLA") (sometimes referred to as Photo Refractive Keratectomy ("PRK"), and Small Incision Lenticular Extraction ("SMILE"). Although names can vary in the marketplace most, if not all, laser eye surgeries into one of these forms (the difference being the manufacturer of the technology, the clinic uses, and how they market it).

In this description and in the following claims, Laser-Assisted in SItu Keratomileusis ("LASIK") is defined as a type of refractive surgery for the correction of myopia, hyperopia, and astigmatism. LASIK surgery is performed by an ophthalmologist who uses a laser or microkeratome to reshape the eye's cornea in order to improve visual acuity. For many patients, LASIK provides a permanent alternative to eyeglasses or contact lenses. Different types of LASIK include: Plano-scan-LASIK, Aspheric-LASIK, Tissue-saving-LASIK, Wavefront-guided LASIK, Topography-assisted LASIK, and Bladeless LASIK, During a LASIK procedure, a thin flap in the cornea is created using either a microkeratome blade or a femtosecond laser. The surgeon folds back the flap, then removes some corneal tissue underneath using an excimer laser. The flap is then laid back in place, covering the area where the corneal tissue was removed. With nearsighted people, the goal of LASIK is to flatten the steep cornea; with farsighted people, a steeper cornea is desired. LASIK can also correct astigmatism by smoothing an irregular cornea into a more normal shape.

Aspects of the invention can be used to predict post-operative UCVA after laser eye surgery. Surgery types, surgery parameters, and surgery methods can be selected for a patient based on predicted post-operative UCVA for the patient if the surgery types, surgery parameters, and surgery methods were to be used. Predicting post-operative UCVA can be handled as a regression problem based on patient demography and pre-operative examination details. In an additional aspect, surgery parameters are automatically determined and/or optimized for improved post-operative UCVA by including surgery parameters in a regression model.

While overall patient satisfaction rates after primary LASIK surgery are relatively high, LASIK may not be recommended for everybody. LASIK surgery is costly with potentially no significant improvement for certain types of patients, and possible eye complications after the surgery. A prediction of post-operative UCVA can help patients make an informed decision about investing their money in undergoing a LASIK surgery or not. A prediction of post-operative UCVA can also help surgeons recommend the most promising laser eye surgery type to the patient with customized surgery parameters (e.g., suction time, flap and hinge details, etc.) for the patient.

In general, pre-operative examination results and demographic information for a patient are provided as input to a predictive model. The predictive model uses linear regression to predict post-operative visual acuity for the patient for a variety of different surgery types and/or surgery parameters. The post-operative visual acuity can be predicted for different post-operative times (e.g., one day after surgery, one week after surgery, one month after surgery, etc.).

It can be challenging to take pre-operative examination results and demographic information as input and determine a personalized laser eye surgery recommendation. Large amounts of data about laser eye surgeries is not readily available. Also, there are many pre-operative measurements that can be used as signals. Additionally, examination data can be sparse (i.e., there can be of missing values).

Nonetheless, a predictive model can be formulated from and trained on pre-operative examination results and demographic information from previously conducted laser eye surgeries. For example, operative examination results and demographic information can be obtained for hundreds or even thousands of laser eye surgeries.

Each set of pre-operative examination results can include measured values for any (and potentially all) of: UCVA for one or both eyes, BCVA for one or both eyes, sphere for one or both eyes, axis for one or both eyes, cylinder for one or both eyes, spherical equivalent, slit lamp exam results (e.g., study of eyelids, lashes, conjunctiva, cornea, anterior chamber, pupil, iris, retina, etc.), interocular pressure ("IOP"), retinal exam results (normal or abnormal), eye topography, type of topography machine used, AR sphere, AR cylinder, AR axis, thinnest preoperative corneal thickness, Steep-K (higher diopter number represents steepest meridian of the cornea), Flat-K (lower diopter number represents less steep meridian of the cornea), Axis@Flat-K (1 to 180 degrees), etc.

Demographic data can include any (and potentially all) of patient ID, age, gender, city, etc. Each pre-operative examination can be uniquely identified by the patent ID and examination date.

Domain knowledge can be used to preprocess data by transforming some categorical features into binary features. A categorical feature can be a column in the data which takes any of a number of unique values. For example, topography machine used for the surgery is a categorical feature may take three values (Orbscan, Galilei, or Oculyzer). A binary feature is one that takes two values (0 or 1). Some classification and regression models are not well suited to handing categorical variables. As such, categorical variables can be converted to binary indicator variables.

Surgery name can be a categorical variable with six unique values: FEMTO, C-femto, a-femto, t-femto, repet femto, and plano femto. The categorical feature can be converted into six corresponding binary variables, one each for each of the unique values. Thus, there are now six features to represent surgery name. For an instance of pre-operative examination results, one of the six features has a value of 1 while others have a value of 0.

For some categorical features, domain knowledge can indicate that there may not be one feature per unique value. For example, some unique values have limited value when making a personalized laser eye surgery recommendation. For example, a categorical feature called Retina examination may have any number of different values indicating abnormality, such as, for example, "Chorioretinal Atrophy", "Familial Exudative Vitreo-retinopathy (FEVR)", "Barrage laser done", "Retinal pigment epithelium (RPE) atrophy", "Tilted disc with temporal pallor" or may have the value "normal". When determining a personalized laser eye surgery recommendation for patient, the specific abnormality type may be of limited value. As such, a categorical feature for Retina examination can be transformed into a single binary feature for Retine examination. The binary feature can take values of 0 or 1 for abnormal and normal or vice versa To further fill-in pre-operative examination results, average values can be used to impute missing values for numerical features. Most frequent values can be used to impute missing value for categorical features.

Multiple regression approaches can be evaluated.

FIG. 1 illustrates an example computer architecture 100 that facilitates formulating and training a predictive model to provide personalized refractive surgery recommendations for eye patients. Referring to FIG. 1, computer architecture 100 includes model formulation module 101 and patients 108. Model formulation module 101 and information technology resources storing examination data for patients 108 can be connected to (or be part of) a network, such as, for example, a system bus, a Local Area Network ("LAN"), a Wide Area Network ("WAN"), and even the Internet. Accordingly, model formulation module 101 and information technology resources storing examination data for patients 108 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Model formulation module 101 further includes feature transformer 102, value supplementation module 103, training data creator 106, and model training module 107. Feature transformer 102 is configured to transform values for categorical features into corresponding values for binary features. Value supplementation module 103 is configured to fill in missing values transformed surgery data. Training data creator 106 is configured to generated training data from filled-in surgery data. Model training module 107 is configured to train and formulate predictive models from training data.

Each of patients 108 can be a patient that has undergone laser eye surgery. The laser eye surgeries can be performed by an eye practitioner or by a plurality of different eye practitioners. Surgery data for each laser eye surgery can be stored on information technology resources, for example, at an eye practitioner's office, in a cloud, etc.

Appropriate health care and/or privacy regulations (depending on country) can be followed to collect the surgery data for each laser eye surgery. The collected surgery data can be combined into surgery data 109. Surgery data 109 can include demographic data. However, any personally identifiable information for eye patients can be omitted from surgery data 109. Surgery data 109 may be stored at a storage device (e.g., locally, on cloud resources, etc.) under control of an entity that creates predictive models. Surgery data 109 can be stored in accordance with appropriate health care and/or privacy regulations.

More specifically, surgery data 109 includes, for each laser eye surgery, eye characteristics, demographics, surgery parameters, and UCVA values for an eye patient. For example, examination data 109 includes surgery 111, surgery 121, etc. Surgery 111 includes eye characteristics 112, demographics 113, surgery parameters 114, and UCVA values 116. Similarly, surgery 121 includes eye characteristics 122, demographics 123, surgery parameters 124, and UCVA values 126.

Eye characteristics represent results from a pre-operative examination. Results from a pre-operative eye examination can include pre-operative values for one or more of: UCVA for one or both eyes, BCVA for one or both eyes, sphere for one or both eyes, axis for one or both eyes, cylinder for one or both eyes, spherical equivalent, slit lamp exam results (e.g., study of eyelids, lashes, conjunctiva, cornea, anterior chamber, pupil, iris, retina, etc.), interocular pressure ("IOP"), retinal exam results (normal or abnormal), eye topography, type of topography machine used, AR sphere, AR cylinder, AR axis, thinnest preoperative corneal thickness, Steep-K, Flat-K, Axis@Flat-K, etc.

Demographics can include patient ID, age, gender, city, etc.

Surgery parameters can include a laser eye surgery type and one or more other parameters, such as, for example, flap thickness (100-120 microns), suction time (30-60 second), optic zone (size of treatment area, 6-7 mm), flap diameter, flap side cut angle, and hinge details. Hinge details can include hinge position (e.g., 90), hinge angle (40 to 60 degrees), and hinge width (3 to 4.5 mm).

UCVA values can include one or more UCVA values measured at specified times after laser eye surgery, such as, for example, a UCVA value one day after laser eye surgery, a UCVA value one week after laser eye surgery, and a UCVA value one month after laser eye surgery.

Model formulation module 101 can access surgery data 109. Model formulation module 101 can use surgery data 109 to formulate predictive model 136. Predictive model 136 can predict what type of laser eye surgery provides an eye patient with improved results relative to other types of laser eye surgery. In some aspects, predictive model 136 can also predict what surgery parameters provide an eye patient with improved results relative to other surgery parameters.

Examination data 109 can be initially received at feature transformer 102. Feature transformer 102 can transform one or more (but not necessarily all) categorical features in surgery data 109 into corresponding sets of binary features. Feature transformer 102 can output transformed surgery data 131.

Value supplementation module 103 receives transformed surgery data 131 as input. Value supplementation module 103 imputes values into transformed surgery data 131 for missing values. Value supplementation module 103 can impute average values for missing values for numeric features. Average values can be determined from other values for the same numeric features in other surgery data. Value supplementation module 103 can impute (e.g., most) frequently used values for missing values for categorical features. Frequently used values can be determined from other values for the same categorical features in other surgery data.

Value supplementation module 103 outputs filled-in surgery data 132. Filled-in surgery data 132 includes transformed surgery data with a number of (and potentially all) missing values in surgery data 109 replaced with average or frequently used values. Training data creator 106 receives filled-in surgery data 132 as input.

Training data creator 106 uses filled-in surgery data 132 to create training data 134. Training data 134 can include different forms and types of training data used to train different types of regression models. Training data creator 106 outputs training data 134 including a plurality of training data entries. Model training module 107 receives training data 134 as input.

Training data creator 106 outputs training data 134 including a plurality of training data entries. Model training module 107 receives training data 134 as input. Model training module 107 can use training data 134 formulate and train predictive model 136. Model training module 107 can train on multiple regression models, such as, for example, Gradient Descent Boosted Tree regression, Online Gradient Descent based regression, neural network based regression, Poisson regression, etc.

In one aspect, a Multiple Additive Regression Trees ("MART") gradient boosting algorithm learns an ensemble of regression trees, which is a decision tree with scalar values in its leaves. Functions produced by a regression tree can be piece-wise constant functions. The ensemble of trees is produced by computing, in each part, a regression tree that approximates the gradient of the loss function, and adding it to the previous tree with coefficients that minimize the loss of the new tree. The output of the ensemble produced by MART on a given instance is the sum of the tree outputs. In case of a regression problem, the output is the predicted value of the function.

Eye practitioners can use predictive model 136 to automatically provide personalized laser eye surgery recommendations for patients. Predictive model 136 can be offered to eye practitioners as a Web API, as an application on the web, as a SaaS offering, as an application on mobiles, or any number of other platforms.

Figure 2:
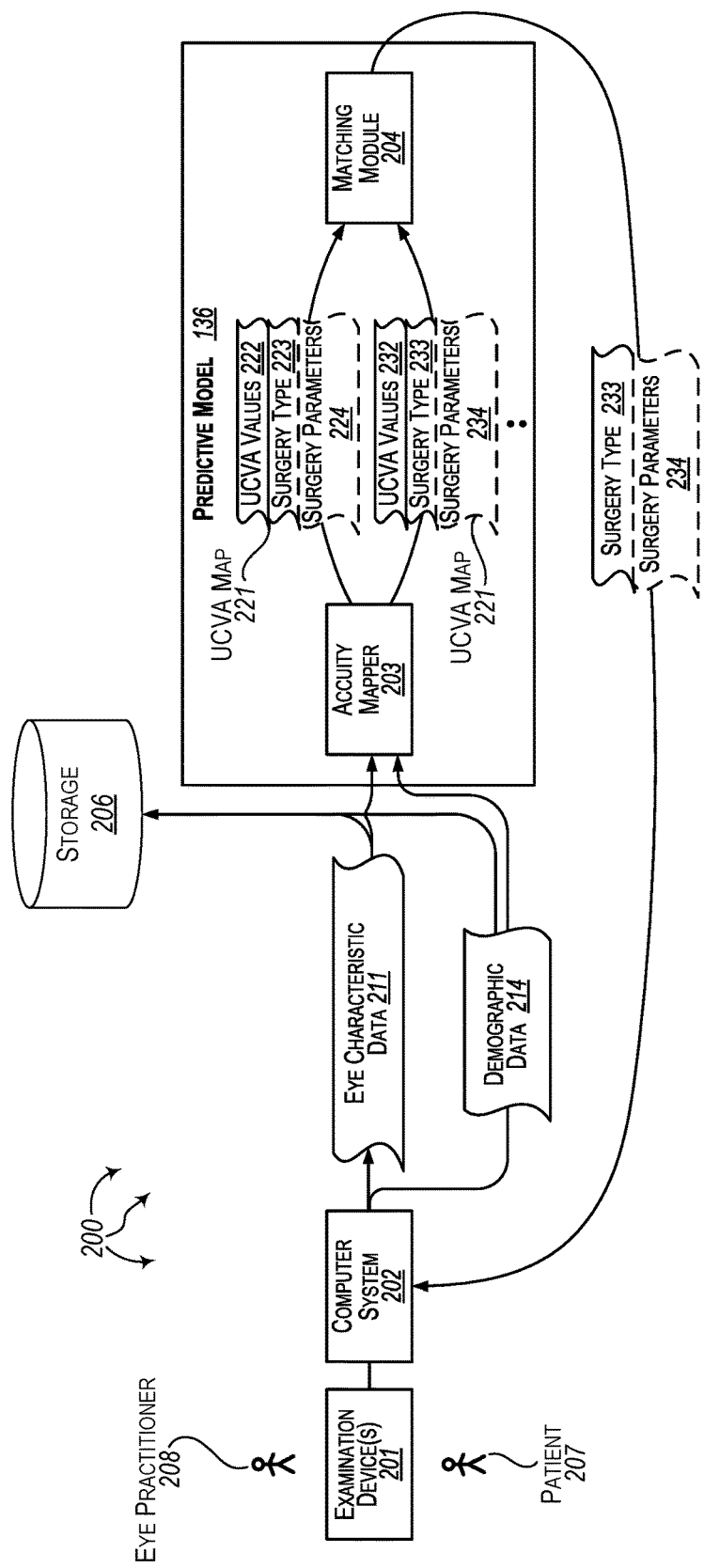
FIG. 2 illustrates an example computer architecture that facilitates providing personalized refractive surgery recommendations for eye patients.

Turning to FIG. 2, FIG. 2 illustrates an example computer architecture that facilitates providing personalized refractive surgery recommendations for eye patients. Referring to FIG. 2, computer architecture 200 includes examination device(s) 201, computer system 202, storage 206, and predictive model 136. Examination device(s) 201, computer system 202, storage 206, and predictive model 136 can be connected to (or be part of) a network, such as, for example, a system bus, a Local Area Network ("LAN"), a Wide Area Network ("WAN"), and even the Internet. Accordingly, examination device(s) 201, computer system 202, storage 206, and predictive model 136 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Predictive model 136 can be run in system memory, such as, for example, system memory of computer system 202 or system memory within cloud resources.

Eye practitioner 208 can perform a pre-operative examination on patient 207. As part of the pre-operative examination, eye practitioner 208 can use examination device(s) 201 to measure and record values for eye characteristics of patient 207. Examination device(s) 201 can (e.g., automatically) send measured values for eye characteristics of patient 207 to computer system 202. Values for various eye characteristics of patient 207 can be recorded in eye characteristics data 211. The various eye characteristics can include one or more of: UCVA for one or both eyes, BCVA for one or both eyes, sphere for one or both eyes, axis for one or both eyes, cylinder for one or both eyes, spherical equivalent, slit lamp exam results (e.g., study of eyelids, lashes, conjunctiva, cornea, anterior chamber, pupil, iris, retina, etc.), interocular pressure ("IOP"), retinal exam results (normal or abnormal), eye topography, type of topography machine used, AR sphere, AR cylinder, AR axis, thinnest preoperative corneal thickness, Steep-K, Flat-K, Axis@Flat-K, etc.

In one aspect, device(s) 201 include a device for generating a topographical map of patient 207's eyes. Eye characteristic data 211 can be derived at least in part from the topographical map. Demographic data for patient 207 (e.g., age, gender, etc.) can be recorded in demographic data 214 at computer system 202. Eye characteristic data 211 and demographic data 214 can be stored in storage 206 (which may be local at eye practitioner 208's office, at a remote storage location, in the cloud, etc.).

Figure 3:
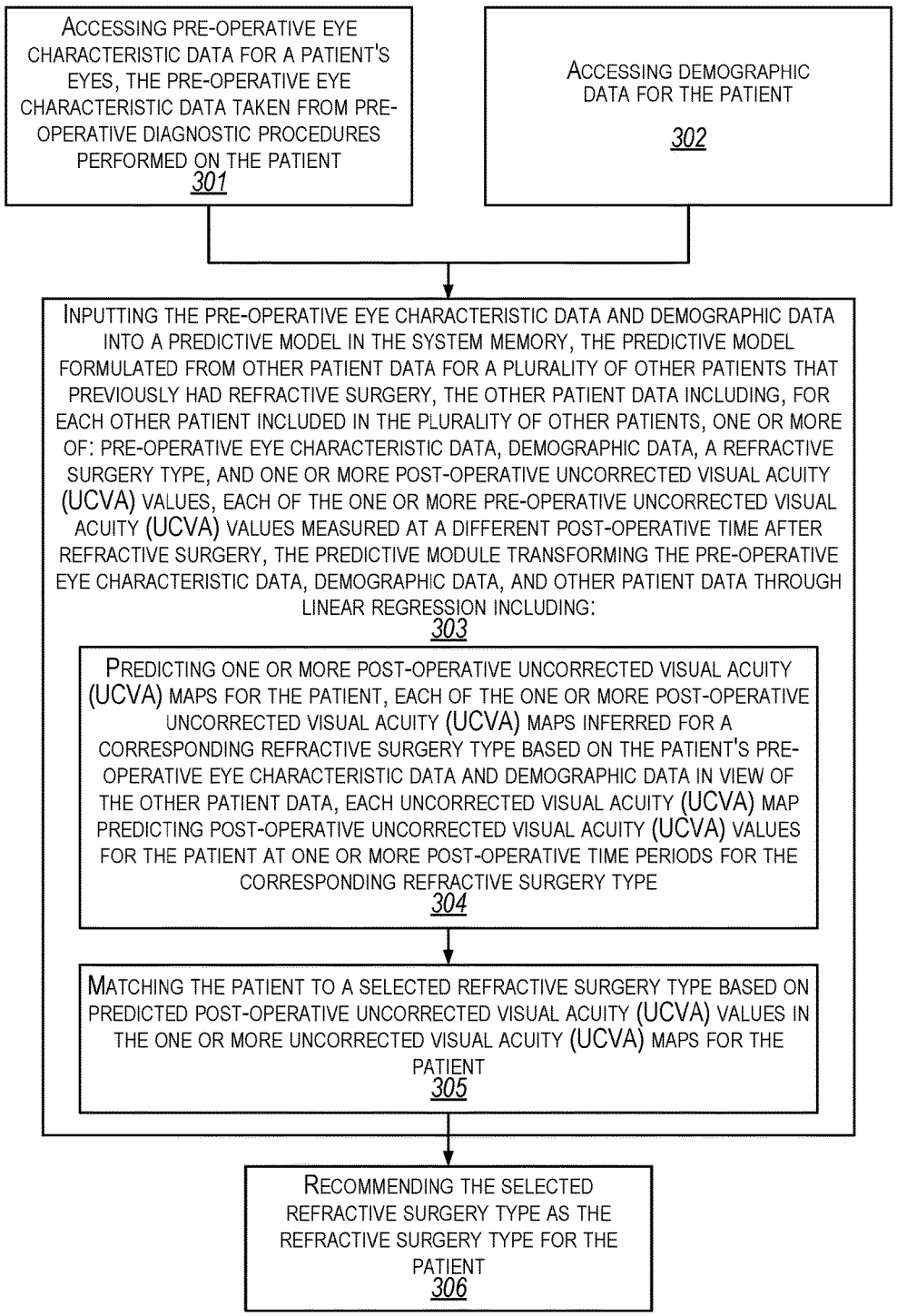
FIG. 3 illustrates a flow chart of an example method for providing personalized refractive surgery recommendations for eye patients.

FIG. 3 illustrates a flow chart of an example method 300 for providing personalized refractive surgery recommendations for eye patients. Method 300 will be described with respect to the components and data of computer architecture 200.

Method 300 includes accessing pre-operative eye characteristic data for a patient's eyes, the pre-operative eye characteristic data taken from pre-operative diagnostic procedures performed on the patient (301). For example, predictive model 136 can access eye characteristic data 211. Method 300 includes accessing demographic data for the patient (302). For example, predictive model 136 can access demographic data 214.

Method 300 includes inputting the pre-operative eye characteristic data and demographic data into a predictive model in the system memory, the predictive model formulated from other patient data for a plurality of other patients that previously had refractive surgery, the other patient data including, for each other patient included in the plurality of other patients, one or more of: pre-operative eye characteristic data, demographic data, a refractive surgery type, and one or more post-operative uncorrected visual acuity (UCVA) values, each of the one or more pre-operative uncorrected visual acuity (UCVA) values measured at a different post-operative time after refractive surgery, the predictive model transforming the pre-operative eye characteristic data, demographic data, and other patient data through linear regression (303). For example, eye characteristic data 211 and demographic data 214 can be input to acuity mapper 203.

Transforming the pre-operative eye characteristic data, demographic data, and other patient data through linear regression includes predicting one or more post-operative uncorrected visual acuity (UCVA) maps for the patient, each of the one or more post-operative uncorrected visual acuity (UCVA) maps inferred for a corresponding refractive surgery type based on the patient's pre-operative eye characteristic data and demographic data in view of the other patient data, each uncorrected visual acuity (UCVA) map predicting post-operative uncorrected visual acuity (UCVA) values for the patient at one or more post-operative time periods for the corresponding refractive surgery type (304). For example, acuity mapper 203 can predict UCVA map 221, UCVA map 231, etc. for patient 207.

Each of UCVA map 221, UCVA map 231, etc. is inferred for a corresponding type of refractive surgery based on eye characteristic data 211 and demographic data 214. For example, UCVA map 221 is inferred for surgery type 223, UCVA map 231 is inferred for surgery type 233, etc. UCVA map 221 predicts post-operative UCVA values 222 for patient 207 at one or more post-operative time periods (e.g., one day, one week, and one month) for the surgery type 223. Similarly, UCVA map 231 predicts post-operative UCVA 232 values for patient 207 at one or more post-operative time periods (e.g., one day, one week, and one month) for the surgery type 233.

Transforming the pre-operative eye characteristic data, demographic data, and other patient data through linear regression includes matching the patient to a selected refractive surgery type based on predicted post-operative uncorrected visual acuity (UCVA) values in the one or more uncorrected visual acuity (UCVA) maps for the patient (305). For example, matching module 204 can match patient 207 to surgery type 233 based UCVA values 222, 223, etc. UCVA values 232 can indicate an improved outcome (e.g., a lower eye number) over time relative to UCVA values for other surgery types.

Method 300 includes recommending the selected refractive surgery type as the refractive surgery recommendation for the patient (306). For example, matching module 204 can return recommendation 213, of surgery type 233 (e.g., some type of LASIK), to computer system 202. Computer system 202 can present recommendation 213 at a user-interface screen. Eye practitioner 208 and patient 207 can view recommendation 213 at the user-interface screen. A hard copy of recommendation 213 can also be printed for eye practitioner 208 and/or patient 207.

Recommendation 213 can be used to assist eye practitioner 208 in tailoring laser eye surgery for patient 207. For example, eye practitioner can tailor surgery parameters (e.g., flap thickness, suction time, optic zone, flap diameter, flap side cut angle, hinge details, etc.) for surgery type 233.

In one aspect, predictive model 136 also considers surgery parameters when making a personalized refractive surgery recommendation. For example, surgery type 223 and surgery type 233 may be the same type of surgery. However, based on eye characteristic data 211 and demographic data 214, acuity mapper 203 predicts that performing the surgery using surgery parameters 234 provides a better outcome (e.g., lower eye number) over time relative to performing the surgery using surgery parameters 233. As such, matching module 204 also includes surgery parameters 234 in recommendation 213.

In another aspect, examination device(s) 201, computer system 202, and predictive model 136 operate in essentially real-time to provide a laser eye surgery recommendation. Data from examination device(s) 201 are automatically fed into computer system 202. In turn, computer system 202 automatically sends eye characteristic data 211 and demographic data 214 to predictive model 136. Predictive model 136 automatically generates and returns recommendation 213 back to computer system 202. Computer system 202 then automatically displays/prints recommendation 213.

Eye practitioner 208 can follow-up with additional post-operative exams to measure UCVA for patient 207 after laser eye surgery of surgery type 233 (potentially performed with surgery parameters 234). Post-operative exams can occur, one day after laser eye surgery, one week after laser eye surgery, and one month after laser eye surgery. Eye characteristic data 211, demographic data 214, surgery type 233 (and potentially surgery parameters 234), and the measured UCVA values can be provided as feedback to model formulation module 106 and/or are included in surgery data 109. Eye characteristic data 211, demographic data 214, surgery type 233 (and potentially surgery parameters 234), and the measured UCVA values can be used to facilitate further training and refinement of predictive model 136.

Accordingly, aspects of the invention can be used provide a personalized laser surgery recommendation for a patient given pre-operative eye examination and demographic details. Regression models can be used to effectively predict post-operative UCVA values from demographics and eye examination features. Other machine learning methods and other forms of classification and regression can also be used.

In some aspects, a computer system comprises one or more hardware processors and system memory. The one or more hardware processors are configured to execute instructions stored in the system memory to provide a refractive surgery recommendation for a patient.

The one or more hardware processors execute instructions stored in the system memory to access pre-operative eye characteristic data for the patient's eyes. The pre-operative eye characteristic data is taken from pre-operative diagnostic procedures performed on the patient. The one or more hardware processors execute instructions stored in the system memory to access demographic data for the patient.

The one or more hardware processors execute instructions stored in the system memory to input the pre-operative eye characteristic data and demographic data into a predictive model in the system memory. The predictive model formulated from other patient data for a plurality of other patients that previously had refractive surgery. The other patient data includes, for each other patient included in the plurality of other patients, one or more of: pre-operative eye characteristic data, demographic data, a refractive surgery type, and one or more post-operative uncorrected visual acuity (UCVA) values. Each of the one or more pre-operative uncorrected visual acuity (UCVA) values measured at a different post-operative time after refractive. The predictive model is configured to transform the pre-operative eye characteristic data, demographic data, and other patient data through linear regression.

The one or more hardware processors execute instructions stored in the system memory to predict one or more post-operative uncorrected visual acuity (UCVA) maps for the patient. Each of the one or more post-operative uncorrected visual acuity (UCVA) maps is inferred for a corresponding refractive surgery type based on the patient's pre-operative eye characteristic data and demographic data in view of the other patient data. Each uncorrected visual acuity (UCVA) map predicts post-operative uncorrected visual acuity (UCVA) values for the patient at one or more post-operative time periods for the corresponding refractive surgery type.

The one or more hardware processors execute instructions stored in the system memory to match the patient to a selected refractive surgery type based on predicted post-operative uncorrected visual acuity (UCVA) values in the one or more uncorrected visual acuity (UCVA) maps for the patient. The one or more hardware processors execute instructions stored in the system memory to return the selected refractive surgery type as the refractive surgery recommendation for the patient.

Computer implemented methods for performing the executed instructions to (e.g., automatically) provide a refractive surgery recommendation for a patient are also contemplated. Computer program products storing the instructions, that when executed by a processor, cause a computer system to (e.g., automatically) provide a refractive surgery recommendation for a patient are also contemplated.

The present described aspects may be implemented in other specific forms without departing from its spirit or essential characteristics. The described aspects are to be considered in all respects only as illustrative and not restrictive. The scope is, therefore, indicated by the appended claims rather than by the foregoing description. All changes which come within the meaning and range of equivalency of the claims are to be embraced within their scope.

What is claimed:

1. A computer system, the computer system comprising:
one or more hardware processors;
   system memory coupled to the one or more hardware processors, the system memory storing instructions that are executable by the one or more hardware processors;
   the one or more hardware processors executing the instructions stored in the system memory to provide a refractive surgery recommendation for a patient, including the following:
      access pre-operative eye characteristic data for the patient's eyes, the pre-operative eye characteristic data taken from pre-operative diagnostic procedures performed on the patient;
      access demographic data for the patient;
      input the pre-operative eye characteristic data and demographic data into a predictive model in the system memory, the predictive model formulated from other patient data for a plurality of other patients that previously had refractive surgery, the other patient data including, for each other patient included in the plurality of other patients, one or more of: pre-operative eye characteristic data and demographic data, a refractive surgery type, and one or more post-operative uncorrected visual acuity (UCVA) values, each of the one or more post-operative uncorrected visual acuity (UCVA) values measured at a different post-operative time after refractive surgery, the predictive model transforming the pre-operative eye characteristic data and the demographic data of the patient's eye through linear regression to:

predict one or more post-operative uncorrected visual acuity (UCVA) maps for the patient, each of the one or more post-operative uncorrected visual acuity (UCVA) maps inferred for a corresponding refractive surgery type based on the patient's pre-operative eye characteristic data and demographic data in view of the other patient data, each uncorrected visual acuity (UCVA) map predicting post-operative uncorrected visual acuity (UCVA) values for the patient at one or more post-operative time periods for the corresponding refractive surgery type; and match the patient to a selected refractive surgery type based on predicted post-operative uncorrected visual acuity (UCVA) values in the one or more uncorrected visual acuity (UCVA) maps for the patient; and recommend the selected refractive surgery type as the refractive surgery recommendation for the patient.

2. The computer system of claim 1, wherein the one or more hardware processors executing the instructions stored in the system memory to access pre-operative eye characteristic data for the patient's eyes comprises the one or more hardware processors executing the instructions stored in the system memory to access one or more of: uncorrected visual acuity (UCVA), uncorrected near vision, corrected near vision, best-corrected visual acuity (BCVA) with corrective lenses, sphere, cylinder, axis, spherical equivalent, slit-lamp exam results, intraocular pressure, Steep-K, Flat-K, Axis@Flat-K, and corneal thickness.

3. The computer system of claim 1, wherein the one or more hardware processors executing the instructions stored in the system memory to access pre-operative eye characteristic data for the patient's eyes comprises the one or more hardware processors executing the instructions stored in the system memory to access results from topological map of the patient's eyes.

4. The computer system of claim 1, wherein the one or more hardware processors executing the instructions stored in the system memory to recommend the selected refractive surgery type as the refractive surgery recommendation for the patient comprises the one or more hardware processors executing the instructions stored in the system memory to recommend a refractive surgery type selected from among: Plano-scan-LASIK, Aspheric-LASIK, Tissue-saving-LASIK, or Wavefront-Guided-LASIK.

5. The computer system of claim 1, wherein the other patient data further includes surgery parameters for each other patient included in the plurality of other, the surgery parameters used for a refractive surgery of the refractive surgery type performed on the other patient.

6. The computer system of claim 1, further comprising the one or more hardware processors executing the instructions stored in the system memory to transform surgery parameters for a subset of the plurality of other patients through linear regression to predict surgery parameters for the patient, the surgery parameters predicted from surgery parameters used in other refractive surgeries of the selected refractive surgery type.

7. The computer system of claim 6, wherein the one or more hardware processors executing the instructions stored in the system memory to predict surgery parameters for the patient comprises wherein the one or more hardware processors executing the instructions stored in the system memory to predict surgery parameters selected from among: flap thickness, suction time, optic zone, flap diameter, flap side cut angle, and hinge details.

8. The computer system of claim 1, wherein the one or more hardware processors executing the instructions stored in the system memory to transform the pre-operative eye characteristic data, demographic data, and other patient data through linear regression comprises the one or more hardware processors executing the instructions stored in the system memory to transform the pre-operative eye characteristic data, demographic data, and other patient data through one of: gradient tree basting regression, online gradient descent based regression, neural network based regression, or Poisson regression.

9. The computer system of claim 1, further comprising the one or more hardware processors executing the instructions stored in the system memory to perform one or more of:

replace a missing value for a feature in the other patient data with an average value for the feature, the average value for the feature averaged from other values for the feature contained in the other patient data; and replace a missing value for a feature in the other patient data with a most frequently used value for the feature contained in the other patient data.

10. The computer system of claim 9, wherein the predictive model being formulated from other patient data comprises the predictive model being formulated based on one or more categorical features contained in the other patient data, each categorical feature having an enumerated plurality of specified possible values.

11. The computer system of claim 10, further comprising the one or more hardware processors executing the instructions stored in the system memory to transform a categorical feature, from among the one or more categorical features, into a corresponding plurality of binary features collectively representing the categorical feature, each corresponding binary feature representing one of the enumerated plurality of specified possible values for the categorical feature; and wherein the predictive model being formulated based on one or more categorical features comprises the predictive model being formulated based on the corresponding plurality of binary features.

12. The computer system of claim 1, wherein the one or more hardware processors executing the instructions stored in the system memory to recommend the selected refractive surgery type as the refractive surgery recommendation for the patient comprise the one or more hardware processors executing the instructions stored in the system memory to recommend a post-operative uncorrected visual acuity (UCVA) map for the patient, the post-operative uncorrected visual acuity (UCVA) map predicting uncorrected visual acuity (UCVA) for the patient for one or more post-operative time periods after refractive surgery of the selected refractive surgery type.

13. A method for use at a computer system, the method for providing a refractive surgery recommendation for a patient, the method comprising the following: accessing pre-operative eye characteristic data for the patient's eyes, the preoperative eye characteristic data taken from pre-operative diagnostic procedures performed on the patient;

accessing demographic data for the patient;

inputting the pre-operative eye characteristic data and demographic data into a predictive model, the predictive model formulated from other patient data for a plurality of other patients that previously had refractive surgery, the other patient data including, for each other patient included in the plurality of other patients, one or more of: pre-operative eye characteristic data, demographic data, a refractive surgery type, and one or more post-operative uncorrected visual acuity (UCVA) values, each of the one or more post-operative uncorrected visual acuity (UCVA) values measured at a different post-operative time after refractive surgery, the predictive model transforming the pre-operative eye characteristic data and the demographic data of the patient's eye through linear regression, including:

predicting one or more post-operative uncorrected visual acuity (UCVA) maps for the patient, each of the one or more post-operative uncorrected visual acuity (UCVA) maps inferred for a corresponding refractive surgery type based on the patient's pre-operative eye characteristic data and demographic data in view of the other patient data, each uncorrected visual acuity (UCVA) map predicting post-operative uncorrected visual acuity (UCVA) values for the patient at one or more post-operative time periods for the corresponding refractive surgery type; and matching the patient to a selected refractive surgery type based on predicted post-operative uncorrected visual acuity (UCVA) values in the one or more uncorrected visual acuity (UCVA) maps for the patient; and recommending the selected refractive surgery type as the refractive surgery recommendation for the patient.

14. The method of claim 13, wherein accessing pre-operative eye characteristic data for the patient's eyes comprises accessing one or more of: uncorrected visual acuity (UCVA), uncorrected near vision, corrected near vision, best corrected visual acuity (BCVA) with corrective lenses, sphere, cylinder, axis, spherical equivalent, slit-lamp exam results, intraocular pressure, Steep-K, Flat-K, Axis@Flat-K, and corneal thickness.

15. The method of claim 13, further comprising transforming surgery parameters for a subset of the plurality of other patients through linear regression to predict surgery parameters for the patient, the surgery parameters predicted from surgery parameters used in other refractive surgeries of the selected refractive surgery type.

16. The method of claim 15, wherein predicting surgery parameters for the patient comprises predicting surgery parameters selected from among: flap thickness, suction time, optic zone, flap diameter, flap side cut angle, and hinge details.

17. The method of claim 13, wherein the predictive model being formulated from other patient data comprises the predictive model being formulated based on one or more categorical features contained in the other patient data, each categorical feature having an enumerated plurality of specified possible values.

18. The method of claim 17, further comprising transforming a categorical feature, from among the one or more categorical features, into a corresponding plurality of binary features collectively representing the categorical feature, each corresponding binary feature representing one of the enumerated plurality of specified possible values for the categorical feature; and wherein the predictive model being formulated based on one or more categorical features comprises the predictive model being formulated based on the corresponding plurality of binary features.

19. The method of claim 13, wherein recommending the selected refractive surgery type comprises recommending a post-operative uncorrected visual acuity (UCVA) map for the patient, the post-operative uncorrected visual acuity (UCVA) map predicting uncorrected visual acuity (UCVA) for the patient for one or more post-operative time periods after refractive surgery of the selected refractive surgery type.

20. A non-transitory computer-readable storage medium for use at a computer system, the non-transitory computer-readable storage medium comprising computer-executable instructions that, when executed at a processor, cause the computer system to perform a method for providing a refractive surgery recommendation for a patient, the method comprising:

accessing pre-operative eye characteristic data for the patient's eyes, the pre-operative eye characteristic data taken from pre-operative diagnostic procedures performed on the patient;

accessing demographic data for the patient;

inputting the pre-operative eye characteristic data and demographic data into a predictive model, the predictive model formulated from other patient data for a plurality of other patients that previously had refractive surgery, the other patient data including, for each other patient included in the plurality of other patients, one or more of: pre-operative eye characteristic data, demographic data, a refractive surgery type, and one or more post-operative uncorrected visual acuity (UCVA) values, each of the one or more post-operative uncorrected visual acuity (UCVA) values measured at a different post-operative time after refractive surgery, the predictive model transforming the pre-operative eye characteristic data and the demographic data of the patient's eye through linear regression to:

predict one or more post-operative uncorrected visual acuity (UCVA) maps for the patient, each of the one or more post-operative uncorrected visual acuity (UCVA) maps inferred for a corresponding refractive surgery type based on the patient's pre-operative eye characteristic data and demographic data in view of the other patient data, each uncorrected visual acuity (UCVA) map predicting post-operative uncorrected visual acuity (UCVA) values for the patient at one or more post-operative time periods for the corresponding refractive surgery type; and match the patient to a selected refractive surgery type based on predicted post-operative uncorrected visual acuity (UCVA) values in the one or more uncorrected visual acuity (UCVA) maps for the patient; and recommend the selected refractive surgery type as the refractive surgery recommendation for the patient.

* * * * *